United States Patent
Xu et al.

(10) Patent No.: US 6,734,330 B1
(45) Date of Patent: May 11, 2004

(54) CATALYST PRETREATMENT IN AN OXYGENATE TO OLEFINS REACTION SYSTEM

(75) Inventors: Teng Xu, Houston, TX (US); Jeffrey L. White, Cary, NC (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 412 days.

(21) Appl. No.: 09/615,545

(22) Filed: Jul. 13, 2000

Related U.S. Application Data

(63) Continuation-in-part of application No. 09/511,943, filed on Feb. 24, 2000.

(51) Int. Cl.$^7$ .............................................. C07C 2/207
(52) U.S. Cl. ...................... 585/640; 585/638; 585/639
(58) Field of Search ........................ 502/31, 22, 24, 502/62, 85, 156, 208; 585/638, 639, 640

(56) References Cited

U.S. PATENT DOCUMENTS

| | | | |
|---|---|---|---|
| 2,768,127 A | 10/1956 | Kimberlin, Jr. et al. ...... | 196/55 |
| 3,258,455 A | 6/1966 | Natta et al. ................. | 260/93.7 |
| 3,305,538 A | 2/1967 | Natta et al. ................. | 260/93.7 |
| 3,364,190 A | 1/1968 | Emrick ....................... | 260/93.7 |
| 3,645,992 A | 2/1972 | Elston ....................... | 260/80.78 |
| 3,785,782 A | 1/1974 | Cartmell ..................... | 23/288 |
| 4,035,284 A | 7/1977 | Gross et al. ................. | 208/120 |
| 4,062,905 A * | 12/1977 | Chang et al. ................. | 260/682 |
| 4,068,136 A | 1/1978 | Minami ....................... | 307/353 |
| 4,076,698 A | 2/1978 | Anderson et al. ............. | 526/348.6 |
| 4,076,796 A | 2/1978 | Reh et al. ................... | 423/659 |
| 4,134,926 A | 1/1979 | Tsao et al. .................. | 260/682 |
| 4,229,608 A | 10/1980 | Chen et al. .................. | 585/640 |
| 4,243,691 A | 1/1981 | Mohlenkamp, Jr et al. . | 426/649 |
| 4,302,565 A | 11/1981 | Goeke et al. ................. | 526/88 |
| 4,404,095 A | 9/1983 | Haddad et al. ............... | 208/161 |
| 4,419,221 A | 12/1983 | Castagnos, Jr. et al. .... | 208/113 |
| 4,440,871 A | 4/1984 | Lok et al. ................... | 502/214 |
| 4,499,314 A | 2/1985 | Seddon et al. .............. | 585/408 |
| 4,499,327 A | 2/1985 | Kaiser ........................ | 585/640 |

(List continued on next page.)

FOREIGN PATENT DOCUMENTS

| | | | |
|---|---|---|---|
| WO | WO 98/29363 | 7/1998 | ............. C07C/1/20 |

OTHER PUBLICATIONS

Blackwell et al., *Solid–State MNR of Silicoaluminophosphate Molecular Sieves and Aluminophosphate Materials*, J. Phys. Chem., vol. 92, pp. 3965–3970 (1988).
Zenz et al., *Riser Reactor*, Fluidization and Fluid–Particle Systems, Reinhold Publishing Corp. NY, pp. 48–59 (1960).
Kunii et al., *Free Fall Reactor*, Fluidization Engineering, Robert E. Krieger Publishing Co. NY, (1977).
*MTO—has its time come?* Nitrogen & Methanol, No. 246, (Jul.–Aug. 2000).
Barger et al., *Converting Natural Gas to Ethylene and Propylene by the UOP/Hydro MTO Process*, 12$^{th}$ International Zeolite Conference Materials Research Society p. 567–573 (1999).
Chang, *Methanol Conversion to Light Olefins*, Catal. Rev.–Sci. Eng., 26(3&4), 323–345 (1984).
Kaeding et al., *Production of Chemicals from Methanol*, Journal of Catalysis 61, 155–164 (1980).

*Primary Examiner*—Thuan D. Dang

(57) ABSTRACT

Disclosed is a crystalline silicoaluminophosphate molecular sieve comprising a porous framework structure and at least one single ring aromatic compound within the porous framework structure. The silicoaluminophosphate molecular sieve is used to convert oxygenate feed stock to olefin product. The olefin product is high in ethylene and propylene content, with a high selectivity to ethylene. The silicoaluminophosphate molecular sieve can be included with a binder and other materials in finished catalyst form.

25 Claims, 5 Drawing Sheets

DIAGRAM OF THE PULSE REACTOR

U.S. PATENT DOCUMENTS

| Patent No. | | Date | Inventor | Class |
|---|---|---|---|---|
| 4,552,645 A | | 11/1985 | Gartside et al. | 208/80 |
| 4,659,685 A | | 4/1987 | Coleman, III et al. | 502/113 |
| 4,664,888 A | | 5/1987 | Castagnos, Jr. | 422/147 |
| 4,677,242 A | | 6/1987 | Kaiser | 585/638 |
| 4,677,243 A | | 6/1987 | Kaiser | 585/638 |
| 4,752,651 A | | 6/1988 | Kaiser | 585/640 |
| 4,780,196 A | | 10/1988 | Alagy et al. | 208/130 |
| 4,814,067 A | | 3/1989 | Gartside et al. | 208/127 |
| 4,861,743 A | | 8/1989 | Flank et al. | 502/214 |
| 4,861,938 A | | 8/1989 | Lewis et al. | 585/640 |
| 5,071,450 A | * | 12/1991 | Cabrera et al. | 55/66 |
| 5,095,163 A | | 3/1992 | Barger | 585/640 |
| 5,096,684 A | | 3/1992 | Guth et al. | 423/306 |
| 5,098,880 A | * | 3/1992 | Gaffney et al. | 502/432 |
| 5,126,308 A | | 6/1992 | Barger et al. | 502/214 |
| 5,191,141 A | | 3/1993 | Barger et al. | 585/640 |
| 5,343,830 A | | 9/1994 | Alexander et al. | 122/4 |
| 5,714,662 A | | 2/1998 | Vora et al. | 585/640 |
| 5,714,663 A | | 2/1998 | Serrand et al. | 585/648 |
| 5,892,079 A | | 4/1999 | Wilson, Jr. | 556/11 |
| 5,912,393 A | | 6/1999 | Barger et al. | 585/640 |
| 5,925,800 A | | 7/1999 | Sun et al. | 585/640 |
| 5,952,538 A | | 9/1999 | Vaughn et al. | 585/640 |
| 5,972,203 A | | 10/1999 | Smith et al. | 208/113 |
| 6,001,328 A | | 12/1999 | Lillerud et al. | 423/718 |
| 6,023,005 A | | 2/2000 | Lattner et al. | 585/639 |
| 6,046,372 A | * | 4/2000 | Brown et al. | 585/640 |
| 6,048,816 A | * | 4/2000 | Brown et al. | 502/77 |
| 6,051,746 A | * | 4/2000 | Sun et al. | 585/639 |
| 6,121,503 A | | 9/2000 | Janssen et al. | 585/640 |
| 6,121,504 A | | 9/2000 | Kuechler et al. | 585/640 |
| 6,137,022 A | * | 10/2000 | Kuechler et al. | 585/638 |
| 6,166,282 A | | 12/2000 | Miller | 585/638 |
| 6,174,339 B1 | | 1/2001 | Varady | 55/348 |
| 6,316,683 B1 | * | 11/2001 | Janssen et al. | 585/640 |
| 6,437,208 B1 | * | 8/2002 | Kuechler et al. | 585/640 |

* cited by examiner

CATALYST PRETREATMENT IN AN OXYGENATE TO OLEFINS REACTION SYSTEM

RELATED APPLICATIONS

This application is a continuation-in-part of application Ser. No. 09/511,943 filed Feb. 24, 2000, entitled "Catalyst Pretreatment In An Oxygenate to Olefins Reaction System," the entire disclosure of which is hereby incorporated herein by reference.

FIELD OF THE INVENTION

This invention relates to introducing a hydrocarbon into the porous framework of a silicoaluminophosphate molecular sieve. More specifically, this invention is to a silicoaluminophosphate molecular sieve which contains an aromatic compound, and a method for forming said aromatic compound within the porous framework of the silicoaluminophosphate molecular sieve.

BACKGROUND OF THE INVENTION

Demand for polyolefins, e.g., polyethylene and polypropylene, has been steadily increasing. It is projected that the increased demand for polyolefins will outpace the availability of raw materials, e.g., ethylene and propylene, from which polyolefins can be made.

Olefins which are used to make polyolefins have been traditionally produced from petroleum feedstocks by either catalytic or steam cracking of the petroleum. The cost of petroleum cracking has steadily increased, however, making it important to find alternative feedstock sources for olefins.

Oxygenates are a promising alternative feedstock for making olefins. Particularly promising oxygenate feedstocks are alcohols, such as methanol and ethanol, dimethyl ether, methyl ethyl ether, diethyl ether, dimethyl carbonate, and methyl formate. Many of these oxygenates can be produced by fermentation, or from synthesis gas derived from natural gas, petroleum liquids, carbonaceous materials such as coal, recycled plastics, municipal wastes, or any appropriate organic material. Because of the wide variety of sources, oxygenates have promise as an economical source for olefin production.

One way in which olefins can be made is by catalytic conversion. In U.S. Pat. No. 4,499,327, for example, a catalytic process for converting methanol to olefins is disclosed. The catalyst used in that process contains a silicoaluminophosphate molecular sieve.

Of course, it is highly desirable to convert as much of the oxygenate feedstock as possible into as much olefin product as possible. Various methods of doing such have been described. For example, U.S. Pat. No. 4,677,242 describes a method of increasing the amount of ethylene and propylene produced from the catalytic conversion of methanol by adding an aromatic diluent to the methanol. The catalyst that is used in the process contains a silicoaluminophosphate molecular sieve. The use of the diluent is considered to result in an increased amount of ethylene product.

U.S. Pat. No. 4,499,314 discloses a catalytic process for converting methanol to ethylene and para-xylene. The catalyst that is used is ZSM-5. Promoters are used to promote either the formation of aromatics products or olefins products. Benzene, toluene and para-xylene are preferred aromatics promoters. Ethylene, propylene and butenes are preferred olefin promoters.

There remains, nevertheless, a desire to improve the economic attractiveness of the oxygenate conversion process. Catalysts and methods to produce olefins from oxygenates are needed which increase the selectivity of the oxygenate conversion reaction, particularly to ethylene and propylene, without resorting to adding costly product enhancing promoters. In particular, it is desirable to avoid using aromatic olefin promoters to boost selectivity to ethylene and propylene.

SUMMARY OF THE INVENTION

In order to overcome the various problems associated with providing large quantities of olefin product which can ultimately be used in the manufacture of polyolefin compositions, this invention provides a crystalline silicoaluminophosphate molecular sieve comprising a porous framework structure. Within the porous framework structure there is contained a catalytically active integrated hydrocarbon co-catalyst.

In a preferred embodiment, the invention provides a method of making an integrated hydrocarbon co-catalyst, comprising preparing an silicoaluminophosphate molecular sieve having a porous framework structure and contacting said silicoaluminophosphate with a hydrocarbon at conditions effective to form at least said integrated hydrocarbon co-catalyst within the porous framework, wherein said the silicoaluminophosphate has a catalytic activity index for methanol conversion at 250° C. and 40 psia of at least 2.

The integrated hydrocarbon co-catalyst is a carbonaceous material such that the silicoaluminophosphate molecular sieve containing the integrated hydrocarbon co-catalyst has a catalytic activity index for methanol conversion at 250° C. and 40 psia of at least 2. The catalytic activity index is $k/k_{ini}$, where k is the pseudo-first order rate constant for methanol conversion at 250° C. and 40 psia in the presence of the crystalline silicoaluminophosphate molecular sieve and $k_{ini}$ is the pseudo-first order rate constant for methanol conversion at 250° C. and 40 psia by injecting 1 pulse of 3 microliter of methanol in a pre-calcined crystalline silicoaluminophosphate molecular sieve activated by flowing He at 450° C. for 1 hour.

In another embodiment, there is provided a catalyst for converting an oxygenate feedstock to an olefin product. The catalyst comprises a crystalline silicoaluminophosphate molecular sieve having a porous framework structure, and a binder, wherein the porous framework structure contains an integrated hydrocarbon co-catalyst preferably containing a single ring aromatic compound.

In preferred embodiments of the silicoaluminophosphate molecular sieve and catalyst, the aromatic composition exhibits a Solid State Nuclear Magnetic Resonance (SSNMR) spectra having a peak in the 18–22 ppm region and a peak in the 125–140 ppm region. Preferably, the aromatic composition is selected from the group consisting of alkyl substituted, single ring aromatics. Alternatively, if the intensity of the peak in the 18–22 ppm region is negligible, a peak near 128 ppm also indicates the material of this invention. Such a peak represents the presence of benzene, which has the desired effect on catalytic activity, as it rapidly reacts with the oxygenate to make alkylated single ring aromatics. More preferably, the silicoaluminophosphate molecular sieve is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof. The most preferred silicoaluminophosphate molecular sieve is SAPO-34.

Also provided in this invention is a method for making an olefin product from an oxygenate feedstock. The method comprises introducing a hydrocarbon into a porous framework of a silicoaluminophosphate molecular sieve under conditions effective to form an integrated hydrocarbon cc-catalyst preferably containing a single ring aromatic compound, and contacting the silicoaluminophosphate molecular sieve containing the integrated hydrocarbon co-catalyst with an oxygenate feedstock under conditions effective to convert the feedstock to an olefin product. The invention includes the olefin product made according to the described method.

In another preferred embodiment, the invention provides a method wherein the olefin product is contacted with a polyolefin-forming catalyst under conditions effective to form a polyolefin. The invention includes the polyolefin product made according to the described method.

In a more preferred embodiment, there is provided an olefin composition. The olefin composition comprises $C_2$ to $C_4$ hydrocarbons such as ethylene, propylene and butene.

BRIEF DESCRIPTION OF THE DRAWINGS

The present invention will be better understood by reference to the Detailed Description of the Invention when taken together with the attached drawings, wherein.

DETAILED DESCRIPTION OF THE INVENTION

Figure 1:
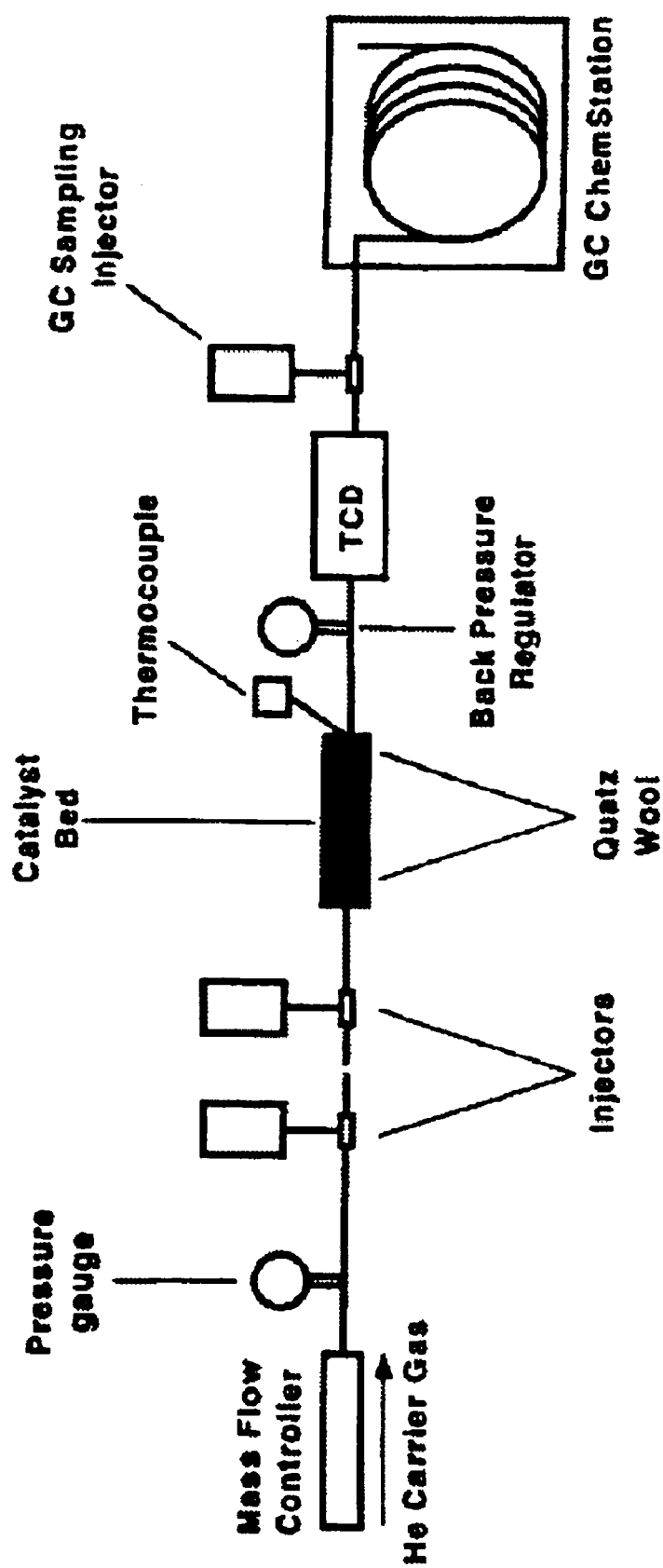
FIG. 1 is a diagram of the pulse reactor for measuring the catalytic activity

Silicoaluminophosphate (SAPO) molecular sieves serve as particularly desirable catalytic materials in converting oxygenate feedstocks to olefin compositions. They are particularly good catalysts for making olefins such as ethylene and propylene from oxygenate compounds.

According to this invention, significant quantities of ethylene and propylene can be produced from oxygenate feedstreams using SAPO molecular sieves if hydrocarbon material is introduced into the porous framework of the silicoaluminophosphate molecular sieves under the appropriate conditions, then contacted with feedstock. Once the silicoaluminophosphate molecular sieve contains a measurable quantity of a catalytically active integrated hydrocarbon co-catalyst, which may be at least one single ring aromatic compound, oxygenate contacting the silicoaluminophosphate molecular sieve at appropriate reaction conditions will be converted to form a product that has a substantial quantity of ethylene and propylene relative to what has been previously achievable. The product will typically be high in ethylene content relative to propylene.

According to this invention, the catalytically active integrated hydrocarbon co-catalyst is a product of a reaction of a hydrocarbon in contact with the porous framework structure of the silicoaluminophosphate molecular sieve and the silicoaluminophosphate has a catalytic activity index for methanol conversion at 250° C. and 40 psia of at least 2, preferably at least 5, more preferably at least 10.

This invention provides a method of making an integrated hydrocarbon co-catalyst, comprising preparing an silicoaluminophosphate molecular sieve having a porous framework structure and contacting said silicoaluminophosphate with a hydrocarbon at conditions effective to form at least said integrated hydrocarbon co-catalyst within the porous framework, wherein said the silicoaluminophosphate has a catalytic activity index for methanol conversion at 250° C. and 40 psia of at least 2, preferably at least 5, more preferably at least 10.

The conditions effective to form at least the integrated hydrocarbon co-catalyst comprises contacting a hydrocarbon having a diameter less than a pore-mouth diameter of the crystalline silicoaluminophosphate molecular sieve. This contacting could comprise first contacting at a lower temperature and second contacting at a higher temperature. The difference between said higher temperature and said lower temperature is at least 10° C., preferably at least 25° C. The hydrocarbon contacted in the first contacting could be different from that contacted in the second contacting.

The oxygenate feedstock of this invention comprises at least one organic compound which contains at least one oxygen atom, such as aliphatic alcohols, ethers, carbonyl compounds (aldehydes, ketones, carboxylic acids, carbonates, esters and the like), and the feedstock may optionally contain at least one compound containing a halide, mercaptan, sulfide, or amine, as long as the optional components do not significantly impede the performance of the catalyst. When the oxygenate is an alcohol, the alcohol can include an aliphatic moiety having from 1 to 10 carbon atoms, more preferably from 1 to 4 carbon atoms. Representative alcohols include but are not necessarily limited to lower straight and branched chain aliphatic alcohols, their unsaturated counterparts and the nitrogen, halogen and sulfur analogues of such. Examples of suitable oxygenate compounds include, but are not limited to: methanol; ethanol; n-propanol; isopropanol; $C_4$–$C_{20}$ alcohols; methyl ethyl ether; dimethyl ether; diethyl ether; di-isopropyl ether, formaldehyde; dimethyl carbonate; dimethyl ketone; acetic acid; and mixtures thereof. Preferred oxygenate compounds are methanol, dimethyl ether, or a mixture thereof.

The method of making the preferred olefin product in this invention can include the process of making these compositions from hydrocarbons such as oil, coal, tar sand, shale, biomass and natural gas. Methods for making the compositions are known in the art. These methods include fermentation to alcohol or ether, making synthesis gas, then converting the synthesis gas to alcohol or ether. Synthesis gas can be produced by known processes such as steam reforming, autothermal reforming and partial oxidization.

One or more inert diluents may be added with the feedstock, for example, in an amount of from 1 to 99 molar percent, based on the total number of moles of all feed and diluent components fed to the reaction zone. For purposes of this invention, diluents are inert compositions that do not participate in the oxygenate conversion reaction, i.e., they are neither created nor consumed. Typical diluents include helium, argon, nitrogen, carbon monoxide, carbon dioxide, water, and mixtures thereof The preferred diluents are water and nitrogen. Water can be injected in either liquid or vapor form.

Hydrocarbons other than oxygenates can also be included as part of the feedstock, i.e., as co-feed. These hydrocarbons can include olefins, paraffins, alkylaromatics, aromatics or mixtures thereof Preferred hydrocarbon co-feeds include, butylene, pentylene, $C_4^+$, $C_5^+$, and mixtures thereof. More preferred as a co-feed is $C_4^+$, with the most preferred being $C_4^+$ which is obtained from separation and recycle of reactor product.

The silicoaluminophosphate molecular sieves of this invention comprise a three-dimensional microporous crystal framework structure of $[SiO_2]$, $[AlO_2]$ and $[PO_2]$ tetrahedral units. The way Si is incorporated into the structure can be determined by $^{29}Si$ MAS NMR. See Blackwell and Patton, *J. Phys. Chem.*, 92, 3965 (1988). The desired SAPO molecular sieves will exhibit one or more peaks in the $^{29}Si$ MAS NMR, with a chemical shift $\delta$ (Si) in the range of −88 to −94 ppm and with a combined peak area in that range of at least 20% of the total peak area of all peaks with a chemical shift $\delta$ (Si) in the range of −88 ppm to −115 ppm, where the $\delta$ (Si) chemical shifts refer to external tetramethylsilane (TMS).

Silicoaluminophosphate molecular sieves are generally classified as being microporous materials having 8, 10, or 12 membered ring structures. These ring structures can have an average pore size ranging from about 3.5–15 angstroms. Preferred are the small pore SAPO molecular sieves having an average pore size ranging from about 3.5 to 5 angstroms, more preferably from 4.0 to 5.0 angstroms. These preferred pore sizes are typical of molecular sieves having 8 membered rings.

In general, silicoaluminophosphate molecular sieves comprise a molecular framework of corner-sharing $[SiO_2]$, $[AlO_2]$, and $[PO_2]$ tetrahedral units. This type of framework is effective in converting various oxygenates into olefin products.

The $[PO_2]$ tetrahedral units within the framework structure of the silicoaluminophosphate molecular sieve of this invention can be provided by a variety of compositions. Examples of these phosphorus-containing compositions include phosphoric acid organic phosphates such as triethyl phosphate, and aluminophosphates. The phosphorous-containing compositions are mixed with reactive silicon and aluminum-containing compositions under the appropriate conditions to form the silicoaluminophosphate molecular sieve.

The $[AlO_2]$ tetrahedral units within the framework structure can be provided by a variety of compositions. Examples of these aluminum-containing compositions include aluminum alkoxides such as aluminum isopropoxide, aluminum phosphates, aluminum hydroxide, sodium aluminate, and pseudoboehmite. The aluminum-containing compositions are mixed with reactive silicon and phosphorus-containing compositions under the appropriate conditions to form the silicoaluminophosphate molecular sieve.

The $[SiO_2]$ tetrahedral units within the framework structure can be provided by a variety of compositions. Examples of these silicon-containing compositions include silica sols and silicium alkoxides such as tetra ethyl orthosilicate. The silicon-containing compositions are mixed with reactive aluminum and phosphorus-containing compositions under the appropriate conditions to form the silicoaluminophosphate molecular sieve.

Substituted SAPOs can also be used in this invention. These compounds are generally known as MeAPSOs or metal-containing silicoaluminophosphates. The metal can be alkali metal ions (Group IA), alkaline earth metal ions (Group IIA), rare earth ions (Group IIIB, including the lanthanoid elements: lanthanum, cerium, praseodymium, neodymium, samarium, europium, gadolinium, terbium, dysprosium, holmium, erbium, thulium, ytterbium and lutetium; and scandium or yttrium) and the additional transition cations of Groups IVB, VB, VIB, VIIB, VIIIB, and IB.

Preferably, the Me represents atoms such as Zn, Mg, M, Co, Ni, Ga, Fe, Ti, Zr, Ge, Sn, and Cr. These atoms can be inserted into the tetrahedral framework through a $[MeO_2]$ tetrahedral unit. The $[MeO_2]$ tetrahedral unit carries a net electric charge depending on the valence state of the metal substituent. When the metal component has a valence state of +2, +3, +4, +5, or +6, the net electric charge is between −2 and +3. Incorporation of the metal component is typically accomplished adding the metal component during synthesis of the silicoaluminophosphate molecular sieve. However, post-synthesis ion exchange can also be used.

Suitable silicoaluminophosphate molecular sieves include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof Preferred are SAPO-18, SAPO-34, SAPO-35, SAPO-44, and SAPO-47, particularly SAPO-18 and SAPO-34, including the metal containing forms thereof, and mixtures thereof. As used herein, the term mixture is synonymous with combination and is considered a composition of matter having two or more components in varying proportions, regardless of their physical state.

The silicoaluminophosphate molecular sieves are synthesized by hydrothermal crystallization methods generally known in the art. See, for example, U.S. Pat. Nos. 4,440,871; 4,861,743; 5,096,684; and 5,126,308, the methods of making of which are fully incorporated herein by reference. A reaction mixture is formed by mixing together reactive silicon, aluminum and phosphorus components, along with at least one template. Generally the mixture is sealed and heated, preferably under autogenous pressure, to a temperature of at least 100° C., preferably from 100–250° C., until a crystalline product is formed. Formation of the crystalline product can take anywhere from around 2 hours to as much as 2 weeks. In some cases, stirring or seeding with crystalline material will facilitate the formation of the product Typically, the silicoaluminophosphate molecular sieve product will be formed in solution. It can be recovered by standard means, however, such as by centrifugation or filtration. The product can also be washed, recovered by the same means and dried.

As a result of the crystallization process, the recovered sieve contains within its pores at least a portion of the template used in making the initial reaction mixture. The crystalline structure essentially wraps around the template, and the template must be removed to obtain catalytic activity. Once the template is removed, the crystalline structure that remains has what is typically called an intracrystalline pore system.

The SAPO molecular sieve can contain one or more templates. Templates are structure directing agents, and typically contain nitrogen, phosphorus, oxygen, carbon, hydrogen or a combination thereon and can also contain at least one alkyl or aryl group, with 1 to 8 carbons being present in the alkyl or aryl group. Mixtures of two or more templates can produce mixtures of different sieves or predominantly one sieve where one template is more strongly directing than another.

Representative templates include tetraethyl ammonium salts, cyclopentylamine, aminomethyl cyclohexane, piperidine, triethylamine, cyclohexylamine, tri-ethyl hydroxyethylamine, morpholine, dipropylamine (DPA), pyridine, isopropylamine and combinations thereof. Preferred templates are triethylamine, cyclohexylamine, piperidine, pyridine, isopropylamine, tetraethyl ammonium salts, and mixtures thereof. The tetraethylammonium salts include tetraethyl ammonium hydroxide (TEAOH), tetraethyl ammonium phosphate, tetraethyl ammonium fluoride, tetraethyl ammonium bromide, tetraethyl ammonium chloride, tetraethyl ammonium acetate. Preferred tetraethyl ammonium salts are tetraethyl ammonium hydroxide and tetraethyl ammonium phosphate.

As is known in the art, molecular sieve or catalyst containing the silicoaluminophosphate molecular sieve, must be activated prior to use in a catalytic process. As used herein the activation of a molecular sieve or a catalyst containing the silicoaluminophosphate molecular sieve means that template is removed from the porous structure of the silicoaluminophosphate molecular sieve, leaving active catalytic sites with the microporous channels of the silicoaluminophosphate molecular sieve open for contact with feed. The activation process is typically accomplished by calcining, or essentially heating the template at a temperature of from 200 to 800° C. in the presence of an oxygen-containing gas. In some cases, it may be desirable to heat in an environment having a low oxygen concentration. This type of process can be used for partial or complete removal of the template from the intracrystalline pore system. In other cases, particularly with smaller templates, complete or partial removal from the sieve can be accomplished by conventional desorption processes such as those used in making standard zeolites.

Once the template has been removed from the silicoaluminophosphate molecular sieve or catalyst containing the silicoaluminophosphate molecular sieve, hydrocarbon material is contacted with the silicoaluminophosphate molecular sieve in a pretreatment zone. The pretreatment zone is operated at conditions effective to form an integrated hydrocarbon co-catalyst which may be at least one single ring aromatic compound within the silicoaluminophosphate molecular sieve. After the an integrated hydrocarbon co-catalyst has been formed, the silicoaluminophosphate molecular sieve is contacted with oxygenate feedstock in a reaction zone under conditions effective to convert the oxygenate to an olefin-containing product. Once the catalyst is pretreated and the an integrated hydrocarbon co-catalyst is formed within the pore structure of the silicoaluminophosphate molecular sieve, it can be allowed to stand for some time in the absence of hydrocarbon or oxygenate feed. It is preferable, however, to maintain the pretreated catalyst in an inert environment if there is to be an extended time before the pretreated catalyst is contacted with oxygenate feed.

The hydrocarbon material contacted with and introduced into the silicoaluminophosphate molecular sieve must be small enough to be adsorbed into the porous framework structure of the silicoaluminophosphate molecular sieve. In general, the hydrocarbon material will comprise at least one hydrocarbon compound which has a kinetic diameter less than the size of the pore mouth opening of the SAPO molecular sieve.

The hidrocarbon material that is contacted with or introduced into the silicoaluminophosphate molecular sieve must be capable of being converted to an integrated hydrocarbon co-catalyst which may be a single ring aromatic compound. The desired aromatic composition cam be identified by Solid State Nuclear Magnetic Resonance (SSNMR) spectra comprising a peak in the 18–40 ppm region and a peak in the 120–150 ppm region. Preferably, the aromatic composition is selected from the group consisting of alkyl substituted, single ring aromatics. Alternatively, if the intensity of the peak in the 18–40 ppm region is negligible, a single peak near 128 ppm also indicates a useful material of this invention, as this indicates the presence of benzene. Benzene also has the desired effect on catalytic activity, as it rapidly reacts with the oxygenate to make alkylated single ring aromatics.

Preferably the an integrated hydrocarbon co-catalyst which may be a single ring aromatic within the silicoaluminophosphate molecular sieve or catalyst containing the silicoaluminophosphate molecular sieve will exhibit a ratio of the intensity of the peak in the 18–40 ppm region to the intensity of the peak in the 120–150 ppm region of not greater than 1.0. More preferably, the an integrated hydrocarbon co-catalyst which may be a single ring aromatic within the silicoaluminophosphate molecular sieve or catalyst containing the silicoaluminophosphate molecular sieve will exhibit a ratio of the intensity of the peak in the 18–40 ppm region to the intensity of the peak in the 120–150 ppm region of between about 0.15 and about 0.7.

It is desirable that the an integrated hydrocarbon co-catalyst which may be a single ring aromatic compound be present within the porous structure of the silicoaluminophosphate molecular sieve in an amount effective to enhance the conversion of oxygenate feed to olefin product, particularly at a concentration effective to enhance selectivity to ethylene and/or propylene. The an integrated hydrocarbon co-catalyst which may be a single ring aromatic can be part of a hydrocarbon composition within the porous structure of the silicoaluminophosphate molecular sieve, and the hydrocarbon composition comprising the an integrated hydrocarbon co-catalyst which may be a single ring aromatic will be present at about 0.1–23 wt% based on the total weight of the silicoaluminophosphate molecular sieve.

Hydrocarbon is introduced into the silicoaluminophosphate molecular sieve by contacting the silicoaluminophosphate molecular sieve or catalyst containing the silicoaluminophosphate molecular sieve with hydrocarbon in a pretreatment zone at conditions effective to form a composition comprising an integrated hydrocarbon co-catalyst which may be at least one single ring aromatic compound within the molecular pore structure of the silicoaluminophosphate molecular sieve. Within the pretreatment zone the conditions are such that an amount of an integrated hydrocarbon co-catalyst which may be a single ring aromatic will be formed with the silicoaluminophosphate molecular sieve pore structure that is effective in enhancing selectivity to ethylene or propylene in an oxygenate to olefin reaction process. The activity of a pretreated catalyst for oxygenate conversion can be expected to increase by a factor of at least about 20% relative to an untreated catalyst. The selectivity to ethylene or propylene of a pretreated catalyst in the oxygenate conversion reaction can be expected to increase by at least about 2 wt. %. Preferably, the an integrated hydrocarbon catalyst which may be a single ring aromatic will occupy at least 0.1 vol. % of the pore structure; more preferably, at least 10 vol. %; most preferably, at least 25 vol. % the molecular pore structure.

In general, the temperature in the pretreatment zone will be less than the temperature in the reaction zone. Desirably, there will be a temperature differential between the reaction zone and the pretreatment zone of greater than or equal to 10° C., preferably greater than or equal to 25° C., more preferably greater than or equal to 50° C., most preferably greater than or equal to about 100° C.

In a preferred embodiment, the temperature in the pretreatment in the pretreatment zone will be not greater than 450° C., more preferably not greater than 400° C., most preferably not greater than 350° C. The preferred range of operation in the pretreatment zone is between 50° C. and 450° C., more preferably between 200° C. and 400° C., most preferably between 250° C. and 350° C.

The pretreatment zone can be contained in a separate pretreatment vessel or within a reactor vessel where the catalytic conversion of oxygenate to olefin takes place. In a preferred embodiment, a separate pretreatment vessel will be used. Typically, the pretreatment vessel will be an auxiliary fluidized bed reactor associated with the oxygenate conversion reactor and regenerator system. The auxiliary reactor is capable of continuously receiving catalyst from the regenerator and subsequently supplying pretreated catalyst to the oxygenate conversion reactor.

When pretreatment is carried out within the same vessel where the catalytic conversion of oxygenate to olefin takes place, two separate temperature zones should be maintained in order to get proper introduction of,hydrocarbon and formation of an integrated hydrocarbon co-catalyst which may be at least one single ring aromatic compound in the silicoaluminophosphate molecular sieve. This can be accomplished by introducing the catalyst to be pretreated into one zone of the oxygenate conversion reactor at one set of conditions in the absence of feed oxygenate, and subsequently introducing the pretreated catalyst and any unreacted pretreating hydrocarbon into an oxygenate conversion zone in fluid communication with the pretreatment zone. The feed oxygenate is then introduced to the oxygenate conversion zone at conditions to effect the oxygenate conversion reaction. Different conditions in the two zones may be maintained through control of the conditions at which the catalyst and feeds are introduced, including temperature, pressure or phase. Optionally, each zone may comprise heating or cooling functions such as steam or cooling water coils.

After pretreatment, the silicoaluminophosphate molecular sieve or catalyst containing the silicoaluminophosphate molecular sieve is contacted with feed containing an oxygenate, and optionally a diluent or a co-feed, at process conditions effective to produce an olefin-containing product. The oxygenate to olefin reaction is carried out in a reaction zone, and the reaction zone is contained within a catalytic reactor.

Typically, the oxygenate feed is contacted with the catalyst when the oxygenate is in a vapor phase. Alternately, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions.

Olefins can generally be produced at a wide range of temperatures. An effective operating temperature range can be from about 200° C. to 700° C. At the lower end of the temperature range, the formation of the desired olefin products may become markedly slow. At the upper end of the temperature range, the process may not form an optimum amount of product. In this invention, however, the oxygenate to olefin reaction process will be carried out a temperature differential between the reaction zone and the pretreatment zone of greater than or equal to 10° C. Preferably, the reaction process will be carried out at a temperature range between 350° C. and 600° C., most preferably between 400° C. and 550° C.

Examples of reactors which can be used in this invention include fluid bed reactors and concurrent riser reactors as described in "Free Fall Reactor," *Fluidization Engineering*, D. Kunii and O. Levenspiel, Robert E. Krieger Publishing Co. NY, 1977, expressly incorporated herein by reference. Additionally, countercurrent free fall reactors may be used in the conversion process as described in U.S. Pat. No. 4,068,136 and "Riser Reactor," *Fluidization and Fluid-Particle Systems*, pages 48–59, F. A. Zenz and D. F. Othmno, Reinhold Publishing Corp., NY 1960, the detailed descriptions of which are also expressly incorporated herein by reference.

When the reactor is a fluidized bed reactor, it is preferred that the reactor have a riser region and a dense fluid bed section. In this embodiment, the regenerated catalyst can be returned to the portion of the reactor above the dense phase region, immediately below the dense phase region, or anywhere between about the top one fourth of the riser region and the bottom one fourth of the dense phase region.

The reaction can take place at a weight hourly space velocity (WHSV) of from 1 $hr^{-1}$ to 1000 $hr^{-1}$. According to this invention, WHSV is defined as the weight of oxygenate, and any hydrocarbon which may be optionally added with the feed, per hour per weight of the silicoaluminophosphate molecular sieve content of the catalyst. Preferred reactors are co-current riser reactors and short contact time countercurrent free-fall reactors in which an oxygenate feedstock can be contacted with a molecular sieve catalyst at a WHSV of at least about 20 $hr^{-1}$, preferably in the range of from about 20 $hr^{-1}$ to 500 $hr^{-1}$, and most preferably in the range of from about 20 $hr^{-1}$ to 250 $hr^{-1}$. Because the catalyst or the feedstock may contain other materials which act as inerts or diluents, the WHSV is calculated on the weight basis of the oxygenate feed, and any hydrocarbon which may be present, and the silicoaluminophosphate molecular sieve contained in the catalyst.

Effective pressures for both the pretreatment and the reaction process range from about 0.1 psia to about 500 psia. Preferred pressures are in the range of about 10 psia to about 250 psia, with the most preferred range being of from about 15 psia to about 200 psia. The foregoing pressures are inclusive of any inert diluent or additional hydrocarbon component, as well as the oxygenate compounds and/or mixtures thereof with hydrocarbon.

The residence time of the feed in the reaction zone may vary from fractions of a second to a number of hours, determined largely by the reaction temperature, the pressure, the silicoaluminophosphate molecular sieve catalyst selected, the WHSV, the phase (liquid or vapor), and the process design characteristics.

In the process of this invention, all or part of the catalyst suffers deactivation as a result of carbonaceous deposits forming on the catalyst during the olefin conversion reaction. The catalyst is, therefore, periodically regenerated by contacting it with a regeneration medium to remove all or part of such carbonaceous deposits. This regeneration may occur periodically within the reactor by ceasing the flow of feed to the reactor, introducing a regeneration medium, ceasing flow of the regeneration medium, and then reintroducing the feed to the fully or partially regenerated catalyst. Regeneration preferably occurs periodically or continuously outside the reactor by removing a portion of the deactivated catalyst to a separate regenerator, and subsequently reintroducing the regenerated catalyst to the reactor. Periodic regeneration may occur at times and conditions needed to maintain a level of activity of the entire catalyst within the reactor.

According to one of the preferred embodiments of this invention, the catalyst containing carbonaceous material is regenerated under conditions effective to obtain a regenerated catalyst having a carbonaceous content of less than 2 wt. %, preferably less than 1.5 wt. %, and most preferably less than 1.0 wt. %. Following regeneration, the catalyst is preferably sent to the pretreatment zone.

In order to make up for any catalyst loss during the regeneration or reaction process, fresh catalyst can be added. Preferably, the fresh catalyst is added to the regenerated catalyst after it is removed from the regenerator, and then both are contacted with hydrocarbon material to form a composition comprising an integrated hydrocarbon co-catalyst which may be a single ring aromatic compound. However, the fresh catalyst can be pretreated independently of the regenerated catalyst, or added directly to the reaction zone without pretreatment.

In a preferred embodiment of the continuous operation, only a portion of the catalyst is removed from the reactor and sent to the regenerator to remove the accumulated carbonaceous deposits that result during the catalytic reaction. In the regenerator, the catalyst is contacted with a regeneration medium containing oxygen or other oxidants. Examples of other oxidants include $O_3$, $SO_3$, $N_2O$, NO, $NO_2$, $N_2O_5$, and mixtures thereof It is preferred to supply $O_2$ in the form of air. The air can be diluted with nitrogen, $CO_2$, or flue gas, and steam may be added. Desirably, the $O_2$ concentration in the regenerator is reduced to a controlled level to minimize overheating or the creation of hot spots in the spent or deactivated catalyst. The deactivated catalyst also may be regenerated reductively with $H_2$, CO, mixtures thereof or other suitable reducing agents. A combination of oxidative regeneration and reductive regeneration can also be employed.

In essence, the carbonaceous deposits are removed from the catalyst during the regeneration process, forming a regenerated catalyst. The regenerated catalyst is then sent to the pretreatment zone for forming an aromatic composition within the silicoaluminophosphate molecular sieve, although some of the regenerated catalyst can be sent directly to the reaction zone for catalytic contact with the feed. Typical regeneration temperatures are in the range of 350–800° C., desirably in the range of 400–750° C. Preferably, regeneration is carried out at a temperature range of 450–700° C.

It is desirable to strip at least some of the volatile organic components which may be adsorbed onto the catalyst or located within its microporous structure prior to entering the regenerator. This can be accomplished by passing a stripping gas over the catalyst in a stripper or stripping chamber, which can be located within the reactor vessel or in a separate vessel. The stripping gas can be any substantially inert medium that is commonly used. Examples of stripping gas are steam, nitrogen, helium, argon, methane, $CO_2$, CO, and flue gas.

It may be desirable to cool at least a portion of the regenerated catalyst to a lower temperature before it is sent to the pretreatment zone or the reaction zone. A heat exchanger located externally to the regenerator may be used to remove some heat from the catalyst after it has been withdrawn from the regenerator. When the regenerated catalyst is cooled, it is desirable to cool it to a temperature which is from about 200° C. higher to about 200° C. lower than the temperature of the catalyst withdrawn from the reactor. More desirably, it is cooled to a temperature from about 10–200° C. lower than the temperature of the catalyst withdrawn from the reactor vessel. This cooled catalyst then may be sent to the pretreatment zone or the reaction zone, or it may be recycled back to the regenerator. Introducing the cooled catalyst into the pretreatment zone, the reaction zone or the regenerator serves to reduce the average temperature in the pretreatment zone, reaction zone or regenerator.

In a preferred embodiment of the invention, an average gas superficial velocity of greater than about 1 meter per second (n/s) is maintained in the reaction zone. Preferably, the average gas superficial velocity is greater than about 2 m/s. More preferably, the average gas superficial velocity is between a range of 2–6 n/s.

As defined herein, gas superficial velocity is the volumetric flow rate of the feedstock (including oxygenate, hydrocarbon, and any diluent)divided by the cross-sectional area of reaction zone. Since feedstock is converted to olefin product while flowing through the reaction zone, the volumetric flow rate of the feedstock varies throughout the reaction zone. In addition, depending upon reactor design, the cross-sectional area of the reaction zone may also vary at any given point within the reactor. Therefore, average gas superficial velocity as used herein represents the average gas superficial velocity throughout the reaction zone.

When the average gas superficial velocity is greater than about 1 m/s, back-mixing of gases in the reaction is minimized. This increases the selectivity to the desired light olefins, i.e., ethylene and/or propylene, and increases the approach to plug flow behavior of the gases flowing through the reaction zone. The velocity profile at a given cross section of the reaction zone is approximately flat and there is little axial diffusion or back-mixing of fluid elements. Ideal plug flow behavior occurs when elements of the homogeneous fluid reactant move through a reaction zone as plugs moving parallel to the reactor axis.

In order to maintain plug flow behavior, as well as achieve relatively isothermal conditions within the reaction zone, it may be beneficial to recirculate a portion of the catalyst exiting the reaction zone to recontact the feed. This recirculation may occur either within the reaction zone or outside the reaction zone. Recirculating the catalyst serves to decrease the temperature differential in the reaction zone by absorbing a portion of the heat generated by the conversion reaction. The temperature differential of the reaction zone is the change in temperature from the inlet to the outlet of the reaction zone. The outlet is the portion of the reaction zone at which the reactants (feed, catalyst and products) pass from the reaction zone to a catalyst disengaging zone. In this preferred embodiment, the temperature differential across the reaction zone is less than about 120° C., which is the practical limit of what could be considered near isothermal conditions in a continuously operating system. Preferably, the temperature differential is maintained at less than about 100° C. More preferably, the temperature differential is less than about 30° C.

Desirably, catalyst is recirculated to contact the feed. Preferably, the rate of catalyst, which comprises molecular sieve and other materials such as binders, fillers, etc., recirculated to contact the feed is from about 1 to about 100 times the total feed rate of oxygenates fed to the reactor. More preferably, the rate of catalyst recirculated to recontact the feed is from about 10 to about 80 times the total feed rate of oxygenates to the reactor, and most preferably from about 10 to 50 times. In a process which includes a separate regenerator, at least a portion of the catalyst in the reactor is desirably removed for regeneration and circulated back to the reactor at a rate of from about 0.1 times to about 10 times the total feed rate of oxygenates to the reactor. Preferably, the rate of recirculation is about 0.2 to 5 times the total feed rate of oxygenates to the reactor, more preferably about 0.3 to 3 times. In a preferred embodiment of the invention, the catalyst from the regenerator is converted to a catalyst comprising an integrated hydrocarbon co-catalyst which may be at least one single ring aromatic compound, and the converted catalyst is sent to the oxygenate reaction zone.

It is desirable to use the olefins produced by this invention to make polyolefins, particularly polyethylene and polypropylene. The olefins produced according to this invention are particularly high in ethylene and propylene content, with a high selectivity to ethylene. The olefins products of this invention are identified by $C_2$–$C_4$ hydrocarbons, including ethylene, propylene and butylene.

The olefins produced by this invention can be easily separated, due to the low amount of undesirable by-products produced, and the separated olefins can be manufactured into polyolefins. Processes for forming polyolefins from olefins are known in the art. Catalytic processes are preferred. Particularly preferred are metallocene, Ziegler/Natta and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691, the catalyst and process descriptions of each being expressly incorporated herein by reference. In general, these methods involve contacting the olefin product with a polyolefin-forming catalyst at a pressure and temperature effective to form the polyolefin product.

A preferred polyolefin-forming catalyst is a metallocene catalyst. The preferred temperature range of operation is between 50 and 240° C. and the reaction can be carried out at low, medium or high pressure, being anywhere within the range of about 1 to 200 bars. For processes carried out in solution, an inert diluent can be used, and the preferred operating pressure range is between 10 and 150 bars, with a preferred temperature range of between 120 and 230° C. For gas phase processes, it is preferred that the temperature generally be within a range of 60 to 160° C., and that the operating pressure be between 5 and 50 bars.

This invention will be better understood with reference to the following examples, which are intended to illustrate specific embodiments within the overall scope of the invention as claimed.

General Experimental Procedure (a) Catalyst Activity Index

The catalyst activity index ($k/k_{ini}$) for methanol conversion at 250° C. and 40 psia was determined using the apparatus shown schematically in FIG. 1. The values of $k_{ini}$ and k were determined as follows.

50 mg of pre-calcined and activated SAPO-34 catalyst (Si/Al=0.19) was loaded into a Pyrex glass tube, 12 mm in o.d. by 120 mm in length. The catalyst was activated by flowing He at 450° C. for 1 hour. The glass tube was attached to a vacuum line and evacuated. The catalyst was dehydrated by heating the catalyst at 250° C. for 1 hr in vacuo. The final pressure was generally less than $10^{-2}$ torr and the final temperature was 250° C.

After dehydration of the catalyst, one pulse of 3 microliter of methanol was passed through the catalyst bed and the conversion of methanol was determined by analyzing a portion of the products by gas chromatography. Subsequently, additional 3 microliter pulses of methanol were added every six minutes and the conversion methanol was determined. Assuming a first order reaction kinetics, the rate constant kw and k were proportional to —In(1-conversion). Therefore, the catalytic activity index was determined by the following equation: $k/k_{ini}$=In(1-conversion)In(1-conversion after first pulse of methanol).

(b) EXAMPLES

In the general procedure, SAPO-34 molecular sieve was contacted with acetone, 2-butene, and methanol, respectively. In each case, 1.0 g of calcined catalyst was loaded into a Pyrex glass tube, 12 mm in o.d. by 120 mm in length. The glass tube was attached to a vacuum line and evacuated. The catalyst was dehydrated by heating the catalyst at 200° C. for 1 hr in vacuo. The final pressure was generally less than $10^{-2}$ torr.

After dehydration of the catalyst, the hydrocarbons were contacted with the catalyst at ambient temperature. The exact loading of the hydrocarbons was measured via a capacitance manometer with a loading of 6 wt % on $CH_2$ basis. The sample was then isolated from the vacuum line and heated to 300° C. and the sample temperature was maintained at 300° C. for 0.5 hr. The hydrocarbon content of the catalyst was determined using a LECO C-200 analyzer. Results indicate that there were about 1–3 wt % integrated hydrocarbon co-catalyst on the catalyst in each case.

Example 1

The silicoaluminophosphate molecular sieve generated by the experimental procedure above was analyzed using SSNMR. The SSNMR spectrum was obtained using single-pulse $^{13}C$ excitation, with high-power $^1H$ decoupling during acquisition. $\Xi/2$ pulses were used for carbon signal excitation, and recycle times between pulses were 20 seconds. Typically, 200 acquisitions (or greater) were signal averaged to obtain the spectrum. Magic-angle spinning speeds were typically 8 kHz. All chemical shifts are reported relative to TMS at 0 ppm, using external calibration on hexamethylbenzene (17.4 ppm vs. TMS).

Figure 2:
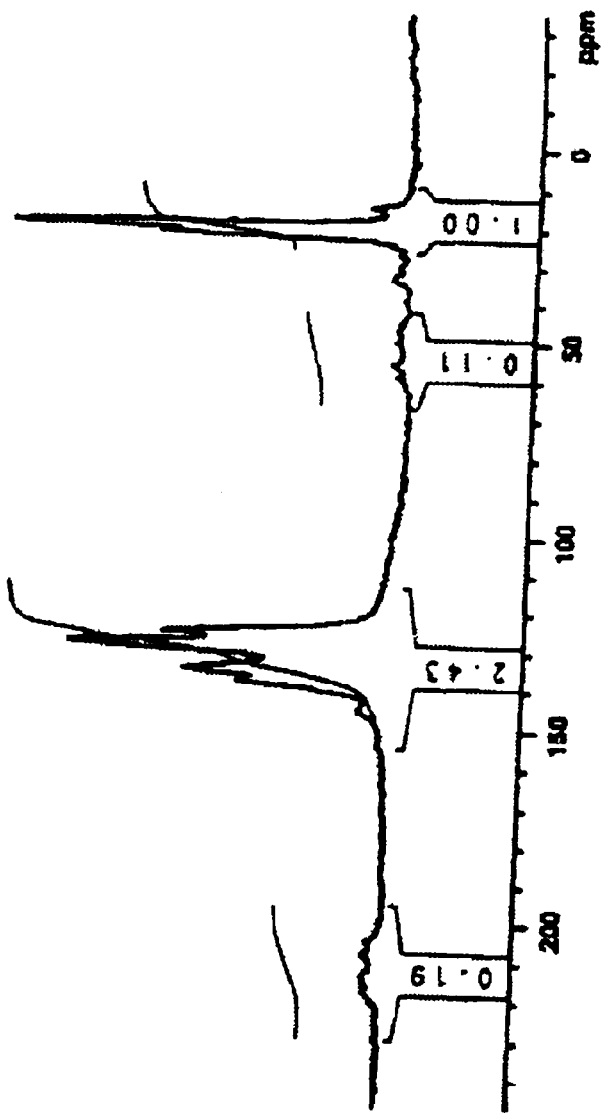
FIG. 2 is a SSNMR spectrum of SAPO-34 catalyst containing alkylated single ring aromatics within the porous framework.

The spectrum for acetone-1,2,3-$^{13}C$ used as a pretreating hydrocarbon on a SAPO-34 catalyst at 250° C. and 260 torr is shown in FIG. 2. There was about 3 wt. % integrated hydrocarbon co-catalyst comprising carbonaceous deposits on the pretreated catalyst following evacuation of the pretreating material. The presence of resolved signals at 134–138 ppm and 19–21 ppm confirm that methyl substituted aromatics result from this preparation scheme. In particular, the spectrum demonstrates that a mixture of alkylated single ring aromatic compounds exist within the silicoaluminophosphate molecular sieve. Chemical shifts for methyl groups observed at 19 and 21 ppm, and aromatic signals at 126, 129, 135 and 138 ppm, support the existence of alkylated aromatic species. Further, the relative integrated intensity of aliphatic region compared to the aromatic region is 0.366. The expected aliphatic to aromatic signal intensity ratio for trimethylbenzenes is 0.500. Thus, the observed value of 0.366 is indicative of a composition in the silicoaluminophosphate molecular sieve comprising primarily xylenes and tri-methylbenzenes.

Figure 3:
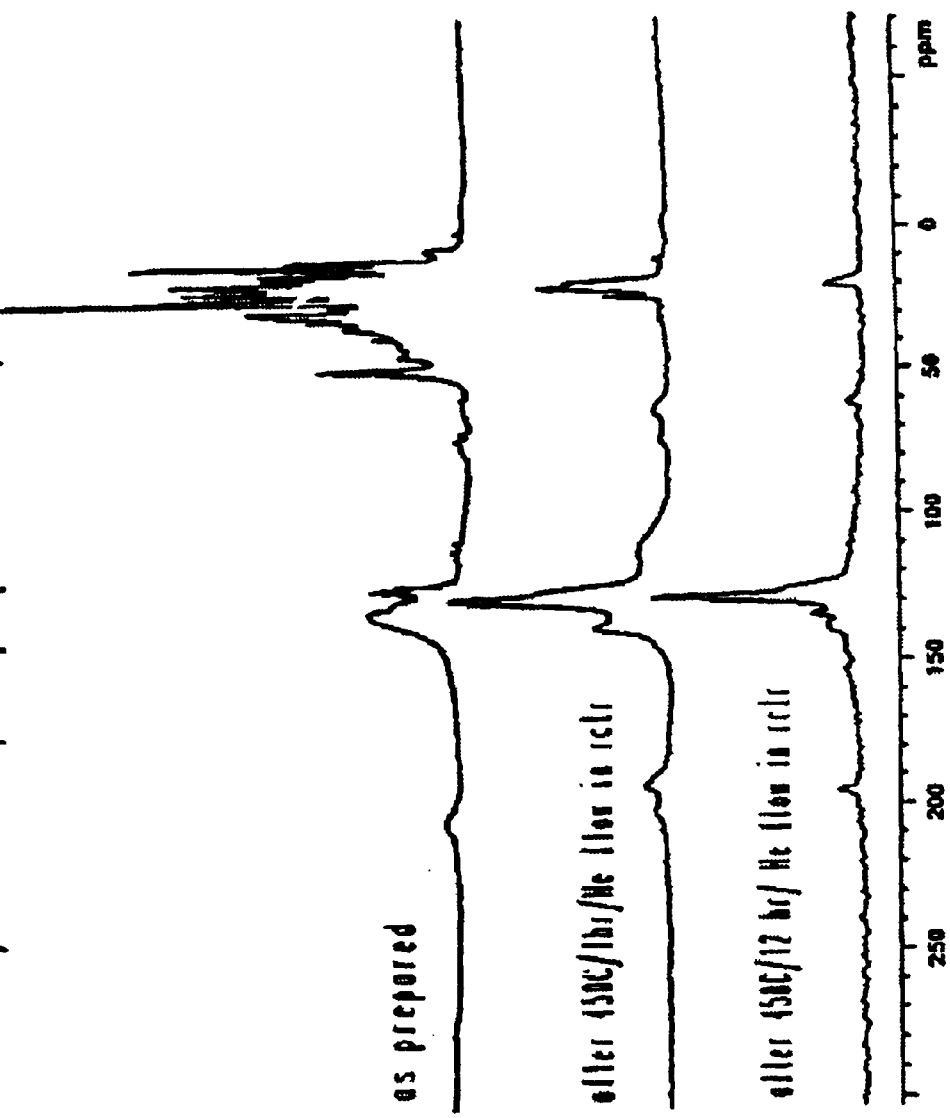
FIG. 3 is a SSNMR spectrum of SAPO-34 catalyst containing various hydrocarbons and alkylated single ring aromatics within the porous framework at various conditions.

The spectra for methanol-$^{13}C$ as a pretreating hydrocarbon for a SAPO-34 catalyst is shown in FIG. 3 The top spectrum, labeled "as prepared," shows the sample pretreated at 300° C. and 260 torr, shortly after the evacuation of pretreating hydrocarbon in the pretreating vessel. The relatively large intensity and distribution of aliphatic signals in the 0–50 ppm region accompanied by a relatively large aliphatic to aromatic signal intensity ratio indicates the presence of substantial aliphatic molecules unattached to aromatics in the pores of the silicoaluminophosphate molecular sieve, and represents the nascent product of the oxygenate conversion reaction at that temperature. The middle spectrum shows the same sample after 1 hour at 450° C. in flowing helium at 40 psia in the absence of any pretreating hydrocarbon or oxygenate feed. In these cases, the aliphatics unattached to single ring aromatics have been removed, revealing the single ring aromatics formed in the silicoaluminophosphate molecular sieve. Longer exposure times in the absence of pretreating materials reduce the aliphatic to aromatic signal intensity ratio, e.g., in the case of the middle spectrum to the case of the bottom spectrum, indicative of the dealkylation of the single ring aromatic species.

Example 2

The production of light olefins was carried out by mixing 50.0 mg of a selected SAPO with 1.0 gram of silicon carbide. The resulting mixture was then placed in a 0.50 inch (outside diameter) No. 304 stainless steel tubular reactor having a wall thickness of 0.063 inch. The tubular reactor was wrapped with electrical heating tape. A thermocouple was provided in direct contact with the catalyst for temperature measurement.

Pure methanol feedstock was introduced to the tubular reactor by means of a Valco four-port injection valve with a fixed volume of 3 Tl concurrently with a stream of helium diluent. The pressure and temperature employed in the example were 40 psia and 450° C., respectively. The effluent from the tubular reactor following each pulse of methanol was collected using a Valco six-port valve with a 2 ml sample loop. The collected effluent sample was analyzed by gas chromatography (Hewlett Packard 6890) equipped with a flame ionization detector. The chromatographic column used was a 150 meter, 0.25 mm (i.d.) fused silica capillary column (Model No. Petrocol DH 150). In between the 3 Tl pulses of methanol feedstock, 50 ml/min of pure helium was run through the reactor at the same conditions. Each point shown in FIGS. 3 and 4 represents the results of the oxygenated conversion reaction for every fifth consecutive pulse of methanol feedstock across the catalysts examined.

Figure 4:
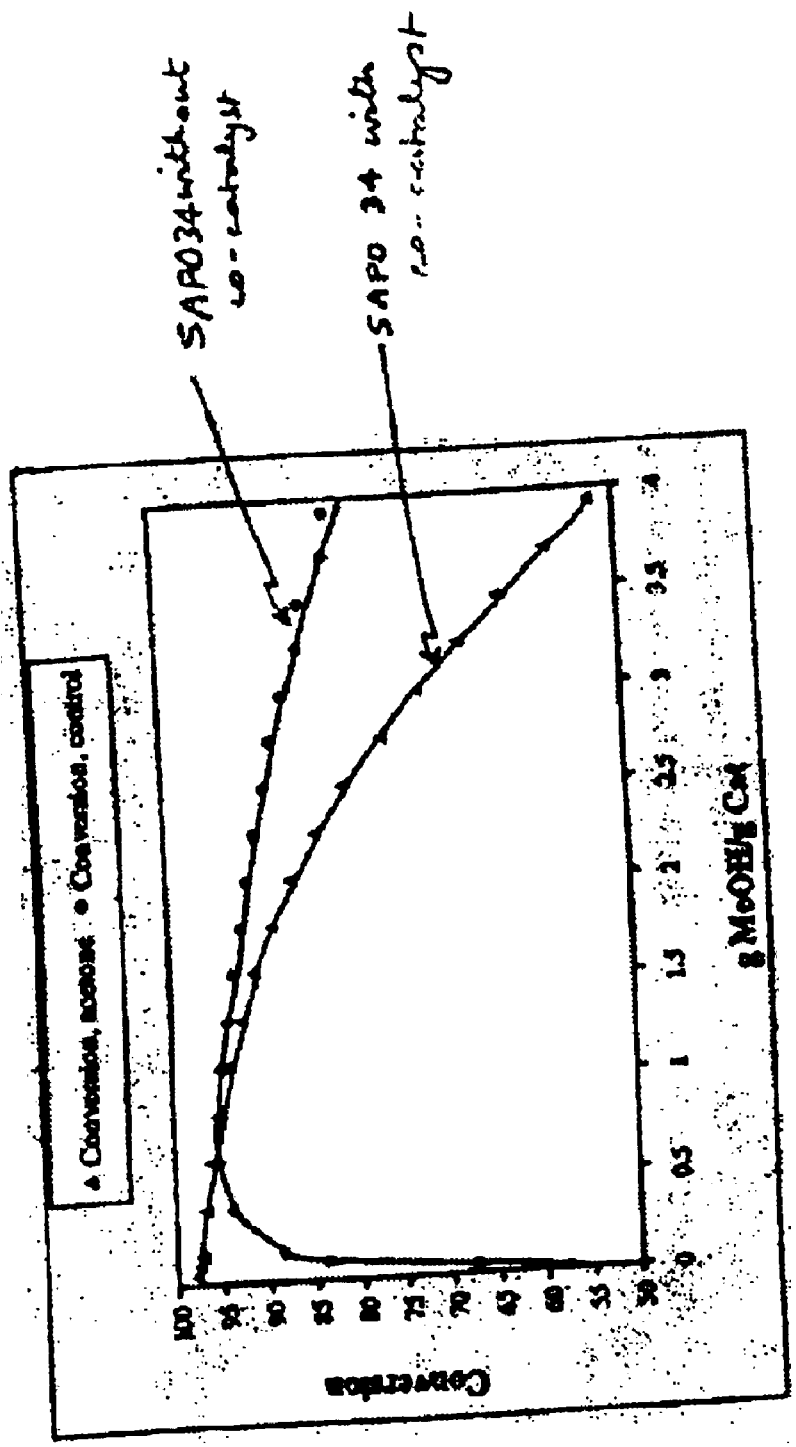
FIG. 4 is a plot comparing conversion of methanol by contacting methanol to SAPO catalysts with and without an integrated hydrocarbon co-catalyst.

FIG. 4 shows the extent of conversion in an oxygenate conversion reaction with methanol feed at 450° C. and 40 psia and WHSV of 25 hr$^{-1}$ utilizing the catalyst prepared from acetone in Example 1, compared to the same SAPO-34 molecular sieve which does not contain alkylated single ring aromatic compounds at the same oxygenate conversion reaction conditions. The increase in activity for methanol conversion for the catalyst of the invention is seen at the initial stages of the reaction.

Figure 5:
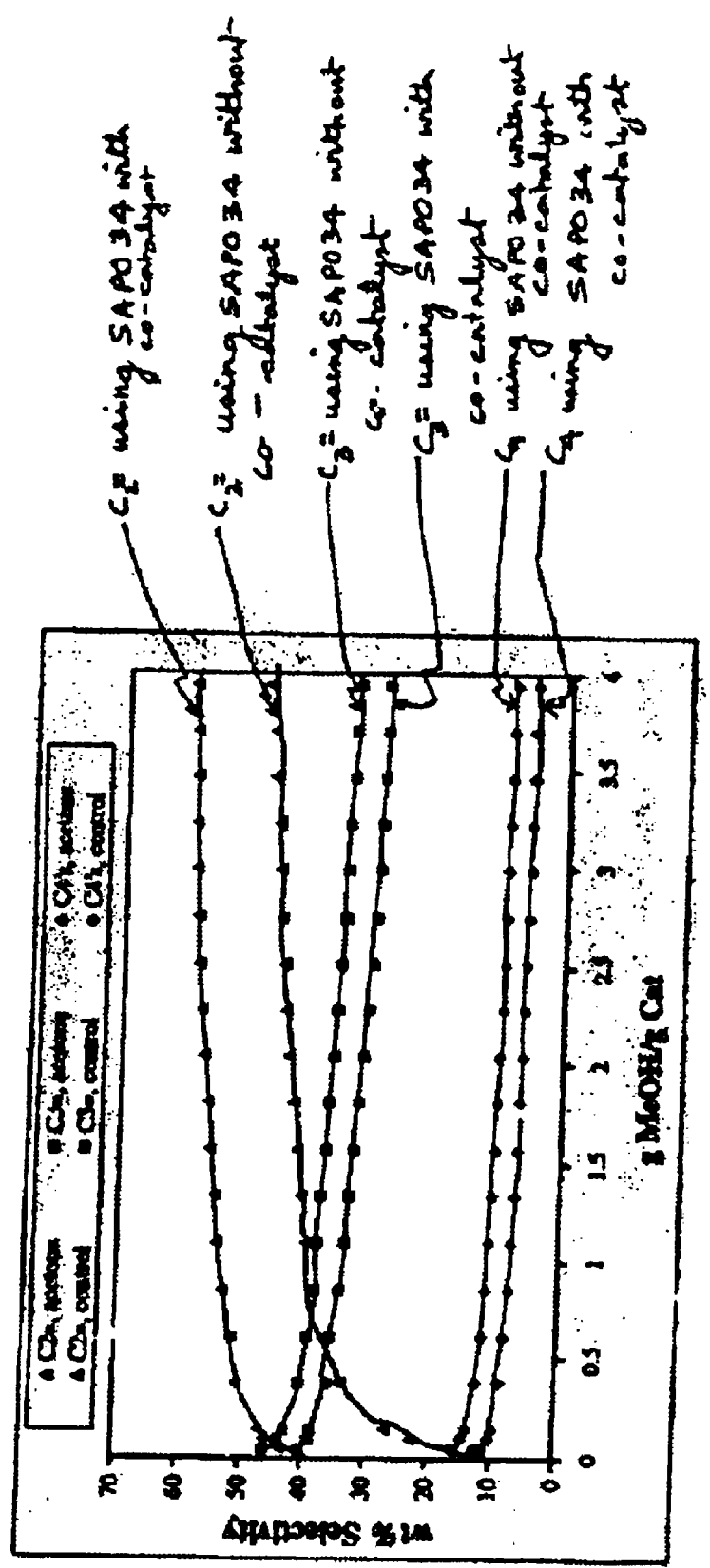
FIG. 5 is a plot of olefin selectivity for methanol reactions by contacting methanol to SAPO catalysts with and without an integrated hydrocarbon co-catalyst.

FIG. 5 shows the selectivity to $C_2$–$C_4$ olefins in the same experiment as described for FIG. 4. The increase in prime olefin selectivity for methanol conversion for the catalyst of the invention, particulary the increase in ethylene selectivity, is shown to be about 10 wt. % or greater at any point in the experiment.

Having now fully described this invention, it will be appreciated by those skilled in the art that the invention can be performed within a wide range of parameters within what is claimed, without departing from the spirit and scope of the invention.

Table 1 shows the catalytic activity increase after the SAPO-34 molecular sieve was loaded with a carbonaceous material.

TABLE 1

| Pretreatment | Activity Increase, $k/k_{1nl}$ | Hydrocarbon Material (wt. %) |
|---|---|---|
| One pulse of 3 μl methanol at 250° C. | 1 | — |
| 30 pulses of 3 μl methanol at 250° C. | 45 | — |
| 90 pulses of 3 μl methanol at 250° C. | 115 | — |
| 25 pulses of 100 μl propene at 350° C. | 38 | 1.9 |
| 25 pulses of 100 μl 1-butene at 350° C. | 67 | — |
| 4 pulses of 100 μl 1-butene at 450° C. | 9 | — |
| 5 pulses of 100 μl 1-butene at 350° C. and 4 pulses of 100 μl 1-butene at 450° C. | 40 | — |
| 25 pulses of 100 μl 2-butene at 350° C. | 84 | 2.0 |
| 10 pulses of 1 μl 1-pentene at 350° C. | 36 | 1.1 |
| 10 pulses of 1 μl 3-hexene at 350° C. | 24 | — |

What is claimed:

1. A method of making an olefin product from a oxygenate feedstock, comprising:
    (a) contracting a silicoaluminophosphate molecular sieve having a porous framework structure with a hydrocarbon at conditions effective to form at least an integrated hydrocarbon co-catalyst within the porous framework, and
    (b) contacting the silicoaluminophosphate molecular sieve containing the integrated hydrocarbon co-catalyst with an oxygenate feedstock under conditions effective to convert the feedstock to the olefin product,
wherein the silicoaluminophosphate molecular sieve has a catalyst activity index for methanol conversion at 250° C. of at least 2.

2. The method of claim 1, wherein the silicoaluminophosphate has a catalytic activity index for methanol conversion at 250° C. of at least 10.

3. The method of claim 1, wherein the catalytically active integrated hydrocarbon co-catalyst is a product of a reaction of any hydrocarbon having a diameter less than a pore-mouth diameter of the crystalline silicoaluminophosphate molecular sieve in contact with the porous framework structure.

4. The method of claim 3, wherein the hydrocarbon comprises an oxygenate.

5. The method of claim 1, wherein the catalytically active integrated hydrocarbon co-catalyst comprises 0.1 to 23 weight percent single ring aromatics.

6. The method of claim 1, wherein the catalytically active integrated hydrocarbon co-catalyst is remains active even after being exposed to air at room temperature for 12 hours or after being subjected to heating at 450° C. for 0.5 hour.

7. The method of claim 1, wherein the silicoaluminophosphate molecular sieve is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof.

8. The process of claim 7, wherein the silicoaluminophosphate molecular sieve is SAPO-34.

9. The method of claim 1, wherein step (a) containing occurs at a lower temperature and step (b) containing occurs at a higher temperature.

10. The method of claim 9, wherein a difference between said higher temperature and said lower temperature is at least 10° C.

11. The method of claim 9, wherein a difference between said higher temperature and said lower temperature is at least 25° C.

12. The method of claim 9, wherein the hydrocarbon contacted in said first contacting is different from that contacted in said second contacting.

13. The method of claim 12, wherein a difference between said higher temperature and said lower temperature is at least 10° C.

14. The method of claim 12, wherein the difference between said higher temperature and said lower temperature is at least 25° C.

15. The method of claim 1, wherein step (a) contacting occurs in a pretreatment zone and step (b) containing occurs in a reaction zone.

16. The method of claim 1, wherein step (a) contacting occurs in a pretreatment vessel and step (b) contacting occurs in a reaction vessel.

17. A method of making a polyolefin from an oxygenate feedstock, comprising:
(a) containing a silicoaluminophosphate molecular sieve having a porous framework structure with a hydrocarbon at conditions effective to form at least an integrated hydrocarbon co-catalyst within the porous framework,
(b) containing the silicoaluminophosphate molecular sieve containing the integrated hydrocarbon co-catalyst with an oxygenate feedstock under conditions effective to convert the feedstock to an olefin product, and
(c) containing the olefin product with a polyolefin-forming catalyst under conditions effective to form the polyolefin, wherein the silicoaluminophosphate molecular sieve containing the integrated hydrocarbon co-catalyst has a catalytic activity index for methanol conversion at 250° C. of at least 2.

18. The method of claim 17, wherein step (a) containing occurs at a lower temperature and step (b) containing occurs at a higher temperature.

19. The method of claim 18, wherein a difference between said higher temperature and said lower temperature is at least 10° C.

20. The method of claim 18, wherein a difference between said higher temperature and said lower temperature is at least 25° C.

21. The method of claim 18, wherein the hydrocarbon contacted in said first contacting is different from that contacted in said second contacting.

22. The method of claim 18, wherein a difference between said higher temperature and said lower temperature is at least 10° C.

23. The method of claim 21, wherein a difference between said higher temperature and said lower temperature is at least 25° C.

24. The method of claim 17, wherein step (a) contacting occurs in a pretreatment zone and step (b) contacting occurs in a reaction zone.

25. The method of claim 17, wherein step (a) contacting occurs in a pretreatment vessel and step (b) contacting occurs in a reaction vessel.

* * * * *